United States Patent [19]

Carr et al.

[11] 4,260,626
[45] Apr. 7, 1981

[54] TETRAHYDRO AND IMIDAZOLINE ANTISECRETORY COMPOUNDS

[75] Inventors: Albert A. Carr; Hsien C. Cheng; Stephen W. Horgan; James K. Woodward, all of Cincinnati, Ohio

[73] Assignee: Richardson-Merrell Inc., Wilton, Conn.

[21] Appl. No.: 23,920

[22] Filed: Mar. 26, 1979

[51] Int. Cl.³ .................................... C07D 233/04
[52] U.S. Cl. ............................. 424/273 R; 424/251; 548/335; 548/341; 544/335
[58] Field of Search ................. 424/251, 273; 544/335; 548/335, 341

[56] References Cited

U.S. PATENT DOCUMENTS

| | | | |
|---|---|---|---|
| 2,919,274 | 12/1959 | Faust et al. | 260/251 |
| 3,657,229 | 4/1972 | Bailey | 544/335 |
| 3,850,957 | 11/1974 | White et al. | 260/309.6 |
| 3,897,431 | 7/1975 | Bailey | 544/335 |
| 3,899,533 | 8/1975 | Souchard | 260/564 G |
| 3,926,994 | 12/1975 | White et al. | 260/251 R |
| 3,965,112 | 6/1976 | White et al. | 260/309.6 |
| 3,996,207 | 12/1976 | White et al. | 260/239 BC |
| 3,998,842 | 12/1976 | White et al. | 260/326.5 B |

FOREIGN PATENT DOCUMENTS 2257784 12/1975 Fed. Rep. of Germany .
49-65629 3/1974 Japan .

OTHER PUBLICATIONS

Faust et al., J. Org. Chem. 26, 4044–4047 (1961).
Dickinson et al., J. Pharmacol. 12, 66–72 (1957).
Neilson et al., J. Chem. Soc. C, 1968 (15), 1853–1856.
Jameson et al., J. Chem. Soc. A, 1968 (4) 921–923.
Ewing et al., J. Chem. Soc., 1965, Jan. 770–774.
Neilson et al., J. Chem. Soc., 1962, 2272–2275.
Bristow, J. Chem. Soc., 1957, 513–515.
Derwent Abstract 44450v, 3-74.
Neilson, CA 70, 42424 (1969).
Tilford et al., JACS 71, 1885 (1949).
Bailey et al., J. Med. Chem. 17 (71702-861974).

*Primary Examiner*—Nicholas S. Rizzo
*Attorney, Agent, or Firm*—John J. Kolano; Raymond A. McDonald; Salvatore R. Conte

[57] ABSTRACT

Novel antisecretory compounds of the formula:

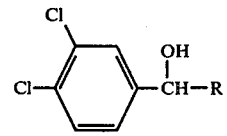

wherein R is wherein R is 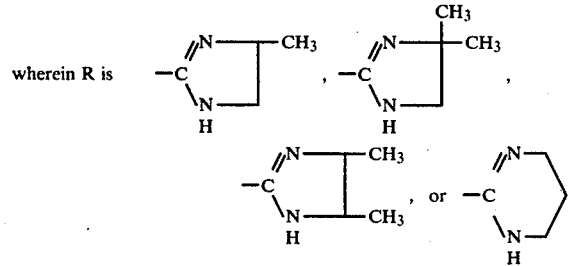

and pharmaceutically acceptable salts, diasteriomers and individual optical isomers thereof.

12 Claims, No Drawings

TETRAHYDRO AND IMIDAZOLINE ANTISECRETORY COMPOUNDS

FIELD OF INVENTION

This invention relates to novel antisecretory compounds, their method of use, and pharmaceutical formulations containing same.

SUMMARY OF INVENTION

Compounds of the following general Formula I and the pharmaceutically acceptable salts, the geometric isomers, where applicable, and individual optical isomers are useful as antisecretory agents:

Formula I

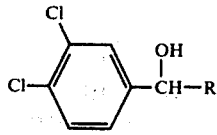

wherein R is

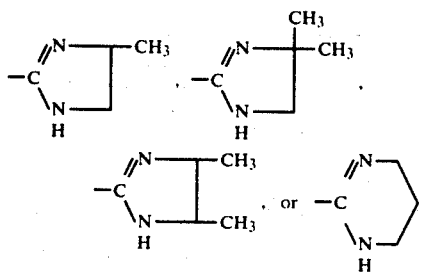

DETAILED DESCRIPTION OF INVENTION

The compounds of the present invention are:

α-(3,4-dichlorophenyl)-4-(or 5)-methyl-2-imidazoline-2-methanol,

α-(3,4-dichlorophenyl)-4,4-(or 5,5)-dimethyl-2-imidazoline-2-methanol,

α-(3,4-dichlorophenyl)-4,5-dimethyl-2-imidazoline-2-methanol, and

α-(3,4-dichlorophenyl)-1,4,5,6-tetrahydro-2-pyrimidine-methanol as represented by the following Formulas II to V, and the pharmaceutically acceptable salts thereof.

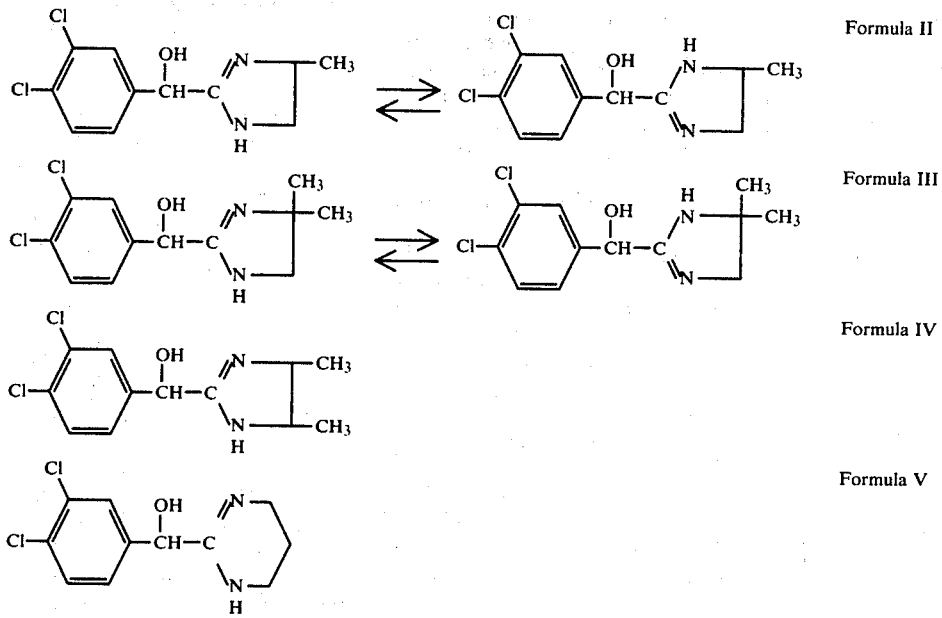

The dotted lines in the hetero ring reflect that the double bond is distributed between the 1- and 2-position in Formulas IIa to Va.

The acid addition salts of the compounds of the present invention in solution and the compounds of the present invention under the conditions of the therapeutic utility may be in tautomeric form as illustrated by the following Formulas IIa to Va. The proportion of each tautomeric form, or the delocalization of the charge between the two nitrogen atoms will be dependent upon various factors for example, the pH of the solution.

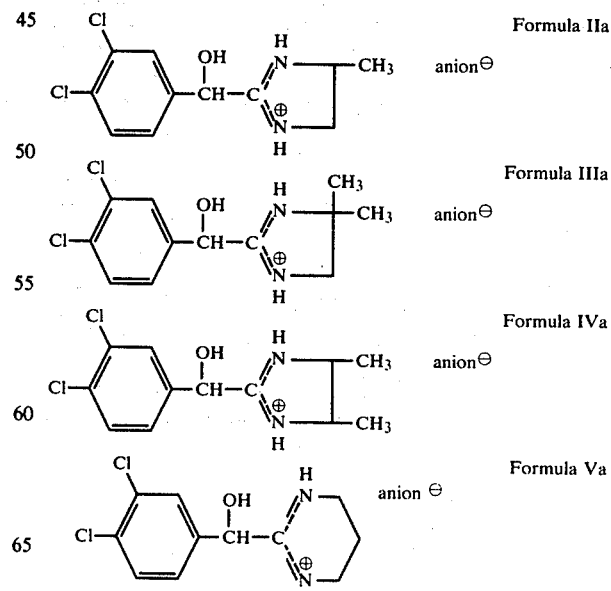

It is understood that this invention encompasses compounds represented or named in either tautomeric form.

The invention also includes the pharmaceutically acceptable acid addition salts of compounds of Formulas I to V which are also useful antisecretory agents. Suitable salts include those of inorganic acids, such as, hydrochloric, hydrobromic, sulfuric and phosphoric acids; carboxylic acids, such as, acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, aminosalicylic, 2-phenoxybenzoic, 2-acetoxybenzoic and mandelic acids; and sulfonic acids, such as, methanesulfonic, 2-hydroxyethanesulfonic and p-toluenesulfonic acids.

It is apparent from Formulas II to V that all of the compounds of the present invention possess an assymetric carbon atom at the methanol carbon of the compounds. Also, it is apparent that the compounds of Formulas II and IV possess additional assymetric carbon atom(s) in the heterocyclic ring at the point of attachment of the methyl group(s). The diastereomers of the compounds of Formulas II and IV and the individual optical isomers of the compounds of Formulas II to V are included within the scope of the present invention.

A preferred embodiment of the present invention is the compound of Formula II, that is, α-(3,4-dichlorophenyl)-5-methyl-2-imidazoline-2-methanol and pharmaceutically acceptable acid addition salts thereof.

The compounds of the present invention are useful as antisecretory agents and therefore are useful in the treatment of conditions due to hypersecretion of gastric acid, for example, peptic ulcers, that is, duodenal, gastric and esophogeal ulcers and in treating Zollinger-Ellison's syndrome. The compounds of the present invention inhibit gastric acid hypersecretion and in practising the present invention can be used therapeutically or prophylactically. The compounds of the present invention are thus useful in preventing hypersecretion of gastric acid and also are useful in treating the conditions resulting from gastric acid hypersecretion. The compounds of the present invention are particularly unique and useful as antisecretory agents being essentially devoid of any α-adrenergic stimulation properties. The compounds of the present invention lack any significant central nervous system properties, such as, sedation and dry mouth syndrome and cardiovascular effects, such as, pressor effects and antihypertensive effects.

The amount of compound employed in practising the present invention can be any antisecretory effective amount which can vary from about 1 mg/kg to 50 mg/kg body weight of the patient per day. A preferred effective amount of compound is about 4 mg/kg to 20 mg/kg body weight of the patient per day. A unit dosage form may contain, for example, about 150 mg of a compound of the present invention and may be administered, for example, from 1 to 4 times daily.

As used herein the term patient is taken to mean warm blooded animals, such as, mammals, for example, rats, dogs, cats, rabbits, and primates, such as, monkeys and humans.

The compounds of the present invention may be administered alone or more preferably in the form of a pharmaceutical preparation. Pharmaceutical compositions containing compounds of the present invention may be in solid or liquid form such as, tablets, capsules, pills, powders, solutions, suspensions, or emulsions and may be administered orally, parenterally, for example, intraperitoneally, intramuscularly, subcutaneously or intravenously or topically, for example, in the form of a suppository. The quantity comprising an effective amount of the novel compound of this invention provided in a unit dosage and the nature and quantity of the pharmaceutically acceptable carrier will vary widely according to the type of pharmaceutical composition and the patient to be treated.

Thus, the solid form can be a capsule which can be of the ordinary gelatin type containing a novel compound of this invention and a carrier, for example, lubricant and inert fillers, such as, lactose, sucrose and corn starch. In another embodiment, the novel compounds are tableted with conventional tablet bases such as lactose, sucrose or corn starch in combination with binders, such as, acacia, corn starch or gelatin, disintegrating agents, such as, corn starch, potato starch or alginic acid and a lubricant such as stearic acid or magnesium stearate. For parenteral administration the compounds may be administered as injectable dosages of a solution or suspension of a compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related solutions, ethanols and glycols, such as, propylene glycol or polyethylene glycol are preferred liquid carriers, particularly for injectable solutions. The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials, such as, biodegradable polymers or synthetic silicones, for example, Silastic, silicone rubber manufactured by the Dow-Corning Corporation.

The following examples are illustrative of suitable pharmaceutical formulations of the compounds of the present invention:

An illustrative composition for tablets is as follows:

|  | Per Tablet |
|---|---|
| (a) α-(3,4-dichlorophenyl)-4-(or 5)-methyl-2-imidazoline-2-methanol hydrochloride | 150.0 mg |
| (b) wheat starch | 15.0 mg |
| (c) lactose | 33.5 mg |
| (d) magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 200 mg each.

An illustrative composition for a parenteral injection is the following wherein the quantities are on a weight to volume basis.

|   | Amount |
|---|---|
| (a) α-(3,4-dichlorophenyl)-4,4-(or 5,5)-dimethyl-2-imidazoline-2-methanol hydrochloride | 150.0 mg |
| (b) peanut oil | 1.5 ml |

The active ingredient is suspended in the oil, and to the suspension is added an appropriate amount of a preservative such as methylparaben or propylparaben.

An illustrative composition for hard gelatin capsules is as follows:

|   | Amount |
|---|---|
| (a) α-(3,4-dichlorophenyl)-4-(or 5)-methyl-2-imidazoline-2-methanol hydrochloride | 200.0 mg |
| (b) talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

The compounds of the present invention are prepared by reacting 1 equivalent of a lower alkyl ester of α-hydroxy-3,4-dichlorobenzeneacetimidic acid acid salt, for example, the ethyl ester hydrochloride salt with an appropriate alkanediamine selected from 1,2-diaminopropane, 2-methyl-1,2-diaminopropane, 2,3-diaminobutane or 1,3-diaminopropane in a lower alcohol solvent, for example, methanol or ethanol at a temperature of from 0° C. to reflux, preferably about 25° C. for 10 minutes to 20 hours. The preferred procedure is to mix the imidate hydrochloride salt and the diamine in methanol for about 30 minutes at about 25° C.

The diastereomers of the compounds of Formulas II and IV are separated by standard techniques well known in the art. The separation procedure consists of standard purification procedures whereby the mixture of diastereomers is recrystallized from any appropriate solvent, that is, a polar solvent which will permit separation of the diastereomers. The individual optical isomers of the compounds of the present invention are separated by resolution with a resolved acid, for example, with d- or l-binaphthyl phosphoric acid or di-p-toluoyl-d-(or l) tartaric acid by procedures well known in the art.

EXAMPLE 1

α-(3,4-Dichlorophenyl)-4-(or 5)-methyl-2-imidazoline-2-methanol hydrochloride

A mixture of 14.2 g (0.05 mole) of ethyl α-hydroxy-3,4-dichlorobenzeneacetimidate hydrochloride, 3.7 g (0.05 mole) of 1,2-diaminopropane and 150 ml of ethanol is stirred for 15 hours at about 25° C. The resultant precipitate is collected, washed with acetone and recrystallized from the methanol/acetone to give α-(3,4-dichlorophenyl)-4-(or 5)-methyl-2-imidazoline-2-methanol hydrochloride, m.p. 209°–212° C.

When in the procedure of Example 1 an appropriate amount of 2-methyl-1,2-diaminopropane, 2,3-diaminobutane or 1,3-diaminopropane is substituted for 1,2-diaminopropane the following respective compounds are obtained:

α-(3,4-dichlorophenyl)-4,4-(or 5,5)-dimethyl-2-imidazoline-2-methanol hydrochloride, m.p. 226°–228° C., α-(3,4-dichlorophenyl)-4,5-dimethyl-2-imidazoline-2-methanol hydrochloride, and α-(3,4-dichlorophenyl)-1,4,5,6-tetrahydro-2-pyrimidine-methanol hydrochloride, m.p. 262°–264° C.

A preferred procedure for the preparation of the compounds of the present invention is illustrated by the following Example 2.

EXAMPLE 2

α-(3,4-Dichlorophenyl)-4-(or 5)-methyl-2-imidazoline-2-methanol hydrochloride

A mixture of 14.2 g (0.05 mole) of ethyl α-hydroxy-3,4-dichlorobenzeneacetimidate hydrochloride, 3.7 g (0.05 mole) of 1,2-diaminopropane and 150 ml of methanol is stirred for 30 minutes at about 25° C. The resultant solution is evaporated to leave a solid residue which is collected, washed with diethyl ether and recrystallized from methanol/butanone to give α-(3,4-dichlorophenyl-4-(or 5)-methyl-2-imidazoline-2-methanol hydrochloride, m.p. 209°–212° C.

Also, further purification of the compounds may be achieved by converting the salt to the free base using, for example, aqueous sodium hydroxide solution. The free base is filtered, washed well with water, dried then converted to the salt, for example, the hydrochloride salt, by using ethereal HCl/methanol. The solvent is removed and the product is recrystallized, for example, with methanol/acetone.

We claim:

1. A compound of the formula

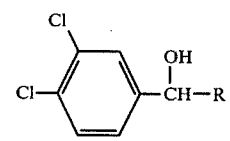

wherein R is

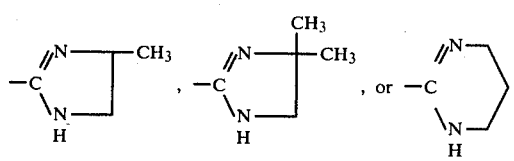

and pharmaceutically acceptable salts, diasteriomers and individual optical isomers thereof.

2. A compound of claim 1 which is α-(3,4-dichlorophenyl)-4-(or 5)-methyl-2-imidazoline-2-methanol or a pharmaceutically acceptable salt thereof.

3. A compound of claim 1 which is α-(3,4-dichlorophenyl)-4-(or 5)-methyl-2-imidazoline-2-methanol hydrochloride.

4. A compound of claim 1 which is α-(3,4-dichlorophenyl)-4,4-(or 5,5)-dimethyl-2-imidazoline-2-methanol or a pharmaceutically acceptable salt thereof.

5. A compound of claim 1 which is α-(3,4-dichlorophenyl)-1,4,5,6-tetrahydro-2-pyrimidinemethanol or a pharmaceutically acceptable salt thereof.

6. A pharmaceutical composition which comprises a compound of claim 1 and a significant amount of a pharmaceutically acceptable carrier.

7. A composition of claim 6 in unit dosage form.

8. A method of preventing the hypersecretion of gastric acid in a patient in need thereof which comprises administering to said patient an effective amount of a compound of claim 1.

9. A method of treating the conditions due to hypersecretion of gastric acid in a patient in need thereof which comprises administering to said patient an effective amount of a compound of claim 1.

10. The method of claim 8 or 9 wherein the effective amount of compound is from 1 mg/kg to 50 mg/kg of body weight of patient per day.

11. The method of claim 8 or 9 wherein the effective amount of compound is from 4 mg/kg to 20 mg/kg of body weight of patient per day.

12. The method of claim 8 or 9 wherein the compound is α-(3,4-dichlorophenyl)-4-(or 5)-methyl-2-imidazoline-2-methanol or a pharmaceutically acceptable salt thereof.

* * * * *